United States Patent [19]
Brodkin et al.

[11] Patent Number: 6,120,591
[45] Date of Patent: Sep. 19, 2000

[54] LOW FUSING DENTAL PORCELAINS CONTAINING FINE-GRAINED LEUCITE

[75] Inventors: Dmitri Brodkin, West Orange; Carl Panzera, Belle Mead; Paul Panzera, Mt. Holly; Jana N. Pruden, Belle Mead; Lisa Kaiser, Monmouth Junction; Richard Brightly, South Brunswick, all of N.J.

[73] Assignee: Jeneric/Pentron Incorporated, Wallingford, Conn.

[21] Appl. No.: 09/133,582

[22] Filed: Aug. 13, 1998

Related U.S. Application Data

[60] Provisional application No. 60/091,527, Jul. 2, 1998, provisional application No. 60/088,866, Jun. 11, 1998, provisional application No. 60/077,555, Mar. 11, 1998, and provisional application No. 60/077,378, Mar. 10, 1998.

[51] Int. Cl.[7] .......................... A61C 13/083; C03C 8/02; C03C 14/00; C03C 10/10
[52] U.S. Cl. ................... 106/35; 501/6; 501/32; 501/59; 501/66; 501/70; 501/67; 501/72; 433/202.1; 433/201.2; 264/16
[58] Field of Search .......................... 106/35; 433/202.1, 433/201.1; 501/6, 32, 59, 66, 70, 64, 72; 264/16

[56] References Cited

U.S. PATENT DOCUMENTS

| | | | |
|---|---|---|---|
| 3,052,982 | 9/1962 | Weinstein et al. | 106/35 |
| 4,455,383 | 6/1984 | Panzera | 501/6 |
| 4,604,366 | 8/1986 | Kacicz et al. | 501/6 |
| 4,798,536 | 1/1989 | Katz | 433/121.1 |
| 5,173,114 | 12/1992 | Heurtaux | 106/35 |
| 5,314,334 | 5/1994 | Panzera et al. | 433/206 |
| 5,614,330 | 3/1997 | Panzera et al. | 428/692 |
| 5,622,551 | 4/1997 | Erbe et al. | 106/35 |
| 5,653,791 | 8/1997 | Panzera et al. | 501/6 |
| 5,698,019 | 12/1997 | Frank et al. | 106/35 |
| 5,713,994 | 2/1998 | Kramer et al. | 106/35 |

FOREIGN PATENT DOCUMENTS

| | | |
|---|---|---|
| 0 272 745 | 6/1988 | European Pat. Off. |
| 0 544 145 | 6/1993 | European Pat. Off. |
| 0 695 726 | 2/1996 | European Pat. Off. |
| 0 795 311 | 9/1997 | European Pat. Off. |
| WO 97 30678 | 8/1997 | WIPO |

*Primary Examiner*—C. Melissa Koslow
*Attorney, Agent, or Firm*—Ann M. Knab

[57] ABSTRACT

A dental porcelain composition, comprising a glassy matrix and leucite crystallites embedded therein, and having maturing temperatures in the range from about 600° C. to about 885° C. and CTEs in the range from about 11 to about 19, more preferably in the range from about 11.5 to about 18, and most preferably in the range from about 12 to about $17.5 \times 10^{-6}$/°C. (measured from 25° C. to 500° C.). The tetragonal leucite is preferably both fine-grained (i.e, having average diameters of less than about 7 microns) and uniformly-sized. Preferably, the average diameters are less than about 1 to about 3 microns.

25 Claims, No Drawings ic s. Dental ceramics exhibit a wide range of coefficients of thermal expansion, from as low as about $8 \times 10^{-6}/°C$ (e.g., alumina) to as high as about $18 \times 10^{-6}/°C$ (e.g., some leucite-reinforced ceramics).

LOW FUSING DENTAL PORCELAINS CONTAINING FINE-GRAINED LEUCITE

CROSS-REFERENCE TO RELATED APPLICATIONS

This application claims priority to U.S. Provisional application No. 60/091527, filed Jul. 2, 1998, U.S. Provisional Application No. 60/088866, filed Jun. 11, 1998, U.S. Provisional application No. 60/077555, Mar. 11, 1998, and U.S. Provisional application No. 60/077378, filed Mar. 10, 1998, all of which are incorporate herein by reference.

BACKGROUND OF THE INVENTION

1. Field of the Invention

The present invention relates to feldspathic leucite-containing dental porcelain compositions for dental restorations. More particularly, this invention relates to low-fusing dental porcelain compositions useful in the preparation and repair of dental restorations such as porcelain-fused-to-metal restorations, all-ceramic restorations, inlays, onlays, and veneers, wherein the leucite is fine-grained.

2. Brief Description of the Related Art

Porcelain dental restorations, such as crowns, bridges, and the like are highly favored because the porcelains provide strength, wear resistance, and favorable aesthetics. Older porcelain restorations generally comprise at least one porcelain layer on a metal framework, commonly known as porcelain-fased-to-metal ("PFM") restorations. Typically, PFM restorations are fabricated by applying a dental porcelain powder in aqueous slurry to a metal alloy framework, then firing the porcelain at high temperature to form a tight, impervious porcelain layer having the appearance of natural dentition. Those skilled in the art recognize that it is important that the firing temperature of the porcelain be at least 100° C. below the solidus temperature of the alloy used as the metal framework, to prevent melting or distortion of the metal framework. It is further important that the coefficient of thermal expansion (CTE) of the porcelain be only slightly less than that of the metal so that no cracks are produced in the porcelain layer due to thermal expansion mismatch stress occurring during firing and cooling down. Metal alloys heretofore employed in the manufacture of dental restorations have typically possessed moderately high coefficients of thermal expansion ranging from about $13 \times 10^{-6}/°C$ to about $17.5 \times 10^{-6}/°C$, with the exception of titanium, which has a coefficient of thermal expansion of about $9 \times 10^{-6}/°C$.

In commonly assigned U.S. application Ser. No. 08/532,179 filed Sep. 22, 1995, now abandoned, the contents of which are incorporated by reference herein, a dental porcelain composition is described which is amorphous, i.e., single phase, and which possesses a moderately high coefficient of thermal expansion closely matching those of conventional alloys and some ceramics heretofore employed in the manufacture of dental restorations. This composition is advantageously applied to such conventional alloys to provide an extremely smooth, fused glassy surface on the resulting dental restoration.

Newer restorations, however, generally comprise a ceramic core in place of the traditional metal, with at least one additional porcelain layer. These are commonly referred to as "all-ceramic" systems, and can provide even better aesthetics than the metal-porcelain systems. Among all-ceramic systems, high strength porcelains provide a more natural translucency and therefore much improved aesthet- Among the commercially-available all-ceramic systems, many are based on pressable, high-strength feldspathic porcelains, for example pressable leucite-reinforced porcelains commercially available under the trade name "OPC®" from Jeneric®/Pentron®, Inc. (Wallingford, Conn.). These feldspathic glass-ceramics comprise from about 40% to 50% of a discontinuous, evenly dispersed, tetragonal potassium leucite phase, which imparts strength to the dental restoration. Leucite is a crystalline potassium aluminum silicate ($K_2O \cdot Al_2O_3 \cdot 4SiO_2$) which ordinarily has a tetragonal crystal structure at room temperature. Use of tetragonal leucite, also known as "low leucite", is described for reinforcement of feldspathic dental porcelains in U.S. Pat. No. 3,052,982 to Weinstein et al., U.S. Pat. No. 4,604,366 to Kacicz et al., U.S. Pat. No. 4,798,536 to Katz, and U.S. Pat. No. 5,614,330 to Panzera, the entire contents of the foregoing patents being incorporated herein by reference. While well-suited for their intended purposes, prior art porcelains for all-ceramic restorations are available in a limited range of maturing temperatures and CTEs, and contain leucite having at least some coarse-grained morphology, that is, a distribution of grain sizes wherein at least a fraction of the grains are greater than about 10 microns, or even greater than about 20 microns. Such coarse-grained leucite can wear away the opposing natural dentition in the mouth.

There accordingly remains a need in the art for high-strength porcelain systems wherein the maturing temperature is low enough to match that of commercially-available metal frameworks, including gold alloys and porcelain cores, and even more advantageously, wherein the CTE may be adjusted to match a range of metal substructure or all ceramic cores. There particularly remains a need for high-strength porcelain systems having low maturing temperatures, yet higher CTEs, and having a fine-grained leucite crystal structure for reducing wear of the opposing natural dentition. Such porcelains must further be simple and inexpensive to manufacture.

SUMMARY OF THE INVENTION

The above-described drawbacks and deficiencies of the prior art are alleviated by the low-fusing dental porcelain compositions of the present invention comprising a glassy matrix and tetragonal leucite dispersed therein, and having maturing temperatures in the range from about 600° C. to about 885° C., more preferably in the range from about 650° C. to about 875° C. and most preferably in the range from about 675° C. to about 870° C., and CTEs in the range from about 11 to about 19, more preferably in the range from about 11.5 to about 18, and most preferably in the range from about 12 to about $17.5 \times 10^{-6}/°C$. (measured from 25° C. to 500° C.). The tetragonal leucite in accordance with the present invention is preferably both fine-grained (i.e, having average diameters of less than about 7 microns) and uniformly-sized. The compositions are described in more detail below.

In one embodiment of the method of the present invention, a porcelain further comprising fine grain sized tetragonal leucite is combined with at least one frit having a very low maturing temperature in order to produce the porcelain of the present invention. In another embodiment of the method of the present invention, the fine grain sized tetragonal leucite is crystallized from a single glassy frit in the initially amorphous glass by heat-treatment of this starting amorphous glass powder.

The porcelains in accordance with the present invention are especially suitable for use in dental restorations as overlay porcelains in combination with both dental alloys and leucite-reinforced core porcelains such as those available from Jeneric®/Pentron® under the trademark OPC®. The restorations thus produced are both aesthetic and forgiving to natural dentition, in that the presence of fine-grained leucite results in less wear of the opposing dentition.

DETAILED DESCRIPTION OF THE INVENTION

The present invention is directed to a low-fusing dental porcelain comprising a glassy matrix and tetragonal leucite, and having maturing temperatures in the range from about 600° C. to about 885° C., preferably in the range from about 650° C. to about 875° C., and most preferably in the range from about 675° C. to about 870° C., and coefficients of thermal expansion in the range from about 11 to about 19, more preferably in the range from about 11.5 to about 18, and most preferably in the range from about 12 to about $17.5 \times 10^{-6}$/C. (measured from 25° C. to 500° C.).

The tetragonal leucite in accordance with the present invention is preferably both fine-grained and uniformly-sized, in order to prevent wear to the opposing dentition. By "fine-grained" is meant leucite crystallites having average diameters of less than about seven microns, preferably less than about five microns, more preferably between about one and three microns and most preferably less than about two to three microns. Individual leucite grains having greater diameters may of course be present, but the presence of such grains is preferably minimized. As used herein, "diameters" refers to the longest single dimension of the crystallite, regardless of the shape of the crystallite.

The amount of leucite present in the glassy matrix is effective to achieve maturing temperatures in the range from about 600° C. to about 875° C. and coefficients of thermal expansion in the range from about 11 to about $19 \times 10^{-6}$/°C. (measured from 25° C. to 500° C.), and is empirically determined by means known in the art, depending on the size and distribution of the tetragonal leucite, the composition of the glassy matrix, the desired maturing temperature and coefficient of thermal expansion, and the intended use of the porcelain (e.g., as a core or as an overlay porcelain). Generally, the leucite is present in an amount in the range from about 5% to about 65% by weight of the total composition, and preferably in the range from about 5% to about 40% by weight of the total composition. As is mentioned below, inclusion of cesium in the glass composition will minimize the amount of leucite required in order to achieve a higher coefficient of thermal expansion.

In one embodiment of the method of manufacture of the present invention, a first porcelain component comprising fine grain sized tetragonal leucite is combined with at least one second porcelain component having a very low maturing temperature, for example in the range from about 600° C. to about 760° C. The composition of the first porcelain component and the at least one second porcelain component is such that combination of the first and second porcelain compositions yields the compositions given in the Tables below. In general, use of at least two porcelain components, or frits, allows greater control in fine-tuning the coefficient of thermal expansion and maturing temperature of the porcelain composition.

The tetragonal leucite for the first porcelain component may be synthesized by means known in the art, for example by volume crystallization. Thus a mixture of powdered metal oxides or carbonates in the appropriate proportions are blended, for example by ball milling for one to three hours. Nucleation agents such as $P_2O_5$, $P_1$, combinations of MgO, ZnO, $TiO_2$ and the like are optionally added to the metal oxides and/or carbonates before blending in order to control nucleation density. The blended powders are then fused to form a glass melt, the glass is quenched (in water or by other means,) and then heated to an elevated temperature (e.g., 950–1100° C.) for approximately one to six hours, allowing the formation and growth of the crystalline leucite. Alternatively, the powders are fused to form a glass, then directly cooled to the crystallization temperature without intermediate quenching. After leucite formation, the material is then quenched, crushed, and reduced to a fine powder. Volume crystallization is known in the art, being described for example in U.S. Pat. No. 4,455,383 to Panzera and U.S. Pat. No. 4,798,536 to Katz, the contents of which patents are incorporated by reference herein.

Alternatively, the leucite-containing porcelain component may be formed by surface crystallization, wherein a mixture of powdered metal oxides or carbonates in the appropriate proportions (and optional nucleation agents) are blended, for example by ball milling for one to three hours. The powders are then fused to form a glass melt, which is quenched in water or by other means. The quenched glass is then milled to a powder before subjecting the powder to heat treatment in order to form crystallized leucite.

In a second embodiment of the method of the present invention, the dental porcelains are formed by volume crystallization of fine grained leucite from a single porcelain composition as described in connection with the first porcelain component above.

Compositional ranges for the fine grained leucite porcelains in accordance with the present invention are shown in Table 1 below.

TABLE 1

| Component | Range | | | | | | | |
|---|---|---|---|---|---|---|---|---|
| | 1 | 2 | 3 | 4 | 5 | 6 | 7 | 8 |
| $SiO_2$ | 40–65 | 40–65 | 40–65 | 58–65 | 58–65 | 57–66 | 57–66 | 57–66 |
| $Al_2O_3$ | 6–12 | 6–13 | 6–12 | 6–12 | 6–13 | 7–13 | 7–13 | 7–13 |
| $K_2O$ | 5.5–10.5 | 5–15 | 5–15 | 5.5–18 | 5–15 | 7–14.5 | 7–18 | 7–18 |
| $Na_2O$ | 6–12 | 6–12 | 6–12 | 7–12 | 7–12 | 7–12 | 4–12 | 7–12 |
| $Li_2O$ | 1–3 | 1–3 | 0–3 | 1.5–3 | 1.5–3 | 0.3–3 | 0.5–3 | 0–3 |
| $B_2O_3$ | 0.5–4 | 0.5–4 | 0–4 | 0.5–4 | 0.5–4 | * | 0–1 | 0–4 |
| BaO | 0–2 | 0–2 | 0–2 | 0–2 | 0–2 | 0–2 | 0–2 | 0–2 |
| CaO | 0.8–2.5 | 0.8–2.5 | 0–3 | 1.2–2.5 | 1.2–2.5 | 0–3 | 0–3 | 0–3 |

TABLE 1-continued

|  | Range | | | | | | | |
| --- | --- | --- | --- | --- | --- | --- | --- | --- |
| Component | 1 | 2 | 3 | 4 | 5 | 6 | 7 | 8 |
| MgO | 0–7 | 0–7 | 0–4 | 0–7 | 0–7 | 0–7 | 0–7 | 0–7 |
| $Cs_2O$ | 0–5 | 0–5 | 0–5 | 0–3 | 0–3 | 0–5 | 0–5 | 0–5 |
| F | 0–2 | 0–2 | 0–2 | 0–2 | 0–2 | 0–4 | 0–4 | 0–4 |
| $P_2O_5$ | 0–3 | 0–3 | 0–3 | 0–3 | 0–3 | 0–3 | 0–3 | 0–3 |
| $CeO_2$ | 0.1–0.8 | 0.1–0.8 | 0–1 | 0.1–2 | 0.1–2 | 0–1 | 0–1 | 0–1 |
| $Sb_2O_3$ | 0–0.5 | 0–0.5 | 0–1 | 0.1–1 | 0.1–1 | 0–1 | 0–0.5 | 0–1 |
| Acidic flux[1] | 0.5–4 | 0.5–4 | 0.8–4 | 0.5–4 | 0.5–4 | 0.8–4.0 | 0.8–4 | 0.8–4 |
| Alkaline flux[2] | 7–15 | 7–15 | 6–15 | 8.5–15 | 8.5–15 | 7.3–15 | 4.5–15 | 7–15 |
| Additives[3] | 0.5–40 | 0.5–40 | 0.5–40 | 0–5 | 0–5 | 0–5 | 0–5 | 0–5 |

*Component excluded from composition except as unavoidable and unintended contaminant
[1]$B_2O_3$ + F + $P_2O_5$
[2]$Li_2O$ + $Na_2O$
[3]Pigments, opacifying agents, fluorescing agents Additional compositional ranges for the fine grained leucite porcelain in accordance with the present invention are shown in Table II below:

TABLE II

| Component | Range 1 | Range 2 | Range 3 | Range 4 | Range 5 | Range 6 | Range 7 | Range 8 | Range 9 |
| --- | --- | --- | --- | --- | --- | --- | --- | --- | --- |
| $SiO_2$ | 40–65 | 40–65 | 40–65 | 58–65 | 58–65 | 40–47 | 40–47 | 57–66 | 57–66 |
| $B_2O_3$ | 0.5–4 | 0.5–4 | 0–4 | 0.5–4 | 0.5–4 | 0.8–2 | 0.8–2 | — | 0–1 |
| $Al_2O_3$ | 6–12 | 6–13 | 6–13 | 6–12 | 6–13 | 5–8 | 6–13 | 7–13 | 7–12 |
| CaO | 0.8–2.5 | 0.8–2.5 | 0.8–2.3 | 1.2–2.5 | 1.2–2.5 | 0.8–3 | 0.8–3 | 0–3 | 0–3 |
| MgO | — | — | 0–4 | — | — | — | — | 0–7 | 0–7 |
| BaO | — | — | 0–1 | — | — | — | — | — | — |
| $Li_2O$ | 1–3 | 1–3 | 0.5–3 | 1.5–3 | 1.5–3 | 1–3 | 1–3 | 0.5–3 | 0.5–3 |
| $K_2O$ | 5.5–10.5 | 5–15 | 5.5–15 | 5.5–18 | 5–15 | 9–10.5 | 5–15 | 7–14.5 | 7–18 |
| $Na_2O$ | 6–12 | 6–12 | 6–12 | 7–12 | 7–12 | 6–12 | 6–12 | 7–12 | 7–12 |
| $Cs_2O$ | — | — | 0–3 | — | — | — | — | — | 0–5 |
| F | 0–2 | 0–2 | 0–2 | 0–2 | 0–2 | 0–2 | 0–2 | 0–4 | 0–4 |
| $B_2O_3$ + F | 0.5–4.0 | 0.5–4.0 | 0.5–4.0 | 0.5–4.0 | 0.5–4.0 | 0.5–4.0 | 0.5–4.0 | — | — |
| $CeO_2$ | 0.1–0.8 | 0.1–0.8 | 0–1 | 0.1–2 | 0.1–2 | .3–1 | .3–1 | 0–1 | 0–1 |
| $Sb_2O_3$ | — | — | — | — | — | — | — | — | 0–0.5 |

The properties of the porcelain components and compositions can be adjusted by applying well known principles. For example, the coefficient of thermal expansion can be increased, if desired, by increasing the leucite content, and by decreasing the proportion of $SiO_2$ and/or increasing the proportion of the alkali metal oxides. Addition of small quantities of $Cs_2O$, wherein the molar ratio of $Cs_2O/K_2O$ is less than 0.1, may significantly increase the expansion of the resulting porcelain. Accordingly, the leucite content is adjusted downward in order to obtain the same CTE. The presence of the acidic fluxes, that is, $B_2O_3$, $P_2O_5$ or F or their combination wherein $B_2O_3$+F+$P_2O_5$=0.5–4% or –0.8% by weight is necessary to attain the requisite crystallization parameters and/or to lower the maturing temperatures. Alkaline fluxes refers to the total quantity of $Li_2O$+$Na_2O$.

The porcelain in accordance with the present invention comprises or may further comprise other additives known in the art, such as opacifiers, pigments (e.g., chromates, vanadates, and manganates, and the like) and fluorescing agents (e.g., cerium oxide, 0.5–2% $Tb_2O_5$, 0–0.4% $Y_2O_3$., and the like).

The following compositions (percent by weight) in table III are exemplary of the compositions of the dental porcelains of the present invention, showing both the intended use of the composition and whether it was derived from a single frit or two frits:

TABLE III

| Component | Ex. 1 (two frit) | Ex. 2 (two frit) | Ex. 3 (two frit) | Ex. 4 (two frit) | Ex. 5 (single frit) | Ex. 6 (single frit) |
| --- | --- | --- | --- | --- | --- | --- |
| $SiO_2$ | 62.0 | 61.5 | 64.2 | 62.7 | 63.2 | 64.4 |
| $Al_2O_3$ | 11.7 | 9.7 | 9.5 | 10.1 | 9.7 | 9.0 |
| $K_2O$ | 15.8 | 14.0 | 13.5 | 11.0 | 15.3 | 13.8 |
| $Na_2O$ | 4.7 | 6.6 | 8.3 | 10.3 | 7.5 | 8.2 |
| $Li_2O$ | 2.6 | 2.2 | 1.4 | 1.2 | 1.2 | 1.2 |
| $B_2O_3$ | 0.50 | 0.9 | 0 | 1.51 | 0 | 0 |
| BaO | 0 | 0 | 0 | 0 | 0 | 0 |
| CaO | 1.7 | 1.7 | 1.1 | 1.6 | 1.1 | 1.2 |
| MgO | 0.8 | 0.7 | 1.0 | 0.9 | 1.1 | 1.1 |
| F | 0.5 | 0.9 | 1.8 | 1.2 | 1.8 | 2.0 |
| $B_2O_3$ + F | 1.0 | 1.8 | 1.8 | 2.71 | 1.8 | 2.0 |
| $Cs_2O$ | 0 | 2.1 | 0 | 0 | 0 | 0 |
| CTE* | 17.5 | 18.0 | 13.7 | 13.7 | 17.5 | 13.8 |
| Maturing T, ° C. | 857 | 816 | 750–760 | 750–760 | 760 | 737 |
| Wt. % leucite** | 40 | 30 | 7 | 7 | 40 | 10 |

*×$10^{-6}$/° C. measured over 25° C. to 470° C.

The above compositions were calculated based on starting batch compositions. Actual fluorine content may therefore be significantly lower due to volatilization losses during melting. The exact percentages of other components such as $Li_2O$ and $B_2O_3$ may also deviate slightly from these calculated values. $Li_2O$ values were obtained by adding to the amount of $Li_2O$ a factor calculated by multiplying he weight percent of fluorine by 16 and dividing by 38. Other components may or may not be present depending on the particular use and physical requirements of the porcelain. Examples 1, 2, 3, and 4 are formulated using the two-frit method, while Examples 5 and 6 were obtained using surface-driven crystallization of leucite from the ground glass powder of a single frit.

The quantity of leucite in Examples 1 and 2 were measured, and found to be approximately 40% by weight (Example 1) and 30% by weight (Example 2). One of ordinary skill in the art would therefore expect the CTE for Example 1 to be higher than that for Example 2, based in the increased amount of leucite. However, the measured CTEs are 17.5 and 18, respectively. Examples 1 and 2 thus illustrate the principle whereby increasing the weight percent of $Cs_2O$ and the molar ratio of $Cs_2O/K_2O$ to less than 0.1 leads to a composition having less leucite, but a CTE comparable to, or higher than, a composition where more leucite is present. Since even fine-grained leucite wears away opposing dentition, the composition of Example 2 provides particularly low wear of opposing dentition.

The porcelains of Examples 1, 2 and 5 are compatible with OPC® cores and type IV gold alloys having expansions in the range from $16-17.5 \times 10^{-6}/°C$. Porcelains of Examples 3, 4, and 6 are compatible with non-precious alloys, for example alloys having CTEs in the range from $13.6-14.9 \times 10^{-6}/°C$. compatible with the SYNSPAR™ Porcelain System and yellow gold alloys having coefficients of thermal expansion of about $14 \times 10^{-6}/°C$., and all-ceramic cores comprising cubic leucite. The exact CTEs of porcelains of course depend on the range over which the measurements are made. For example, the CTEs for Examples 3 and 4 are about 12.4 (measured over 25–400° C.), about 12.7 (measured over 25–430° C.), about 13.7 (measured over 25–470° C.), and about 13.5 (measured over 25–500° C.). Thus, the porcelains of Examples 3 and 4 are matched to alloys having expansions in the range from about 13.6–14.9 ppm/°C., as well as all-ceramic cores having compatible thermal expansions.

In one embodiment, the porcelain composition of the present invention is fused to a metal alloy framework or all-ceramic core to provide a coating thereon. Suitable alloys include those known in the art having a coefficient of thermal expansion in the range from about 13.2 to about $14.9 \times 10^{-6}/°C$., or in the range from about 16 to about $17.5 \times 10^{-6}/°C$. Suitable all-ceramic cores include, but are not limited to cores available under the trade name OPC™ from Jeneric/Pentron, Wallingford, Conn.; under the trade name EMPRESS™, from Ivoclar; and under the trade name CERPRESS™, from the Dillon, Co., Cranston, R.I. Such restorations commonly have multiple porcelain layers in order to simulate natural teeth, and the porcelain of this invention may be used in any one or a combination of these layers, although it is preferably used as an overlayer. The porcelain layers are applied in the conventional manner, that is, in the form of a paste of the porcelain powder in water over the framework, shaping to the desired shape, and then firing.

In another embodiment, the porcelain is used to fabricate inlays, onlays, or veneers to replace amalgam, gold, or other porcelains. In this embodiment, the porcelain powder in accordance with the present invention is built on a refractory die (for example, the refractory die available from Jeneric/Pentron Inc., Wallingford, Conn. under the trade name SYNVEST™) in the form of an aqueous slurry, and then fired to an appropriate temperature to effect maturation and maturing of the porcelain.

While various descriptions of the present invention are described above, it should be understood that various features can be used singly or in any combination thereof. Therefore, this invention is not to be limited to only the specifically preferred embodiment depicted herein. Further, it should be understood that variations and modifications within the spirit and scope of the invention may occur to those skilled in the art to which the invention pertains. Accordingly, all expedient modifications ready attainable by one versed in the art from the disclosure set forth herein that are within the scope and spirit of the present invention are to by included as further embodiments of the present invention. The scope of the present invention is accordingly defined as set forth in the appended claims.

What is claimed is:

1. A single frit porcelain composition for the manufacture of a dental porcelain, comprising:

40–65% $SiO_2$, 6–13% $Al_2O_3$, 5.5–15% $K_2O$, and 6–12% $Na_2O$, 0.5–3% $Li_2O$, 0–4% $B_2O_3$, 0–2% F, and 0.8–2.3 CaO by weight of the total composition, wherein the weight percent of ($F+B_2O_3$ is in the range from 0.5–4.0, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}/°C$. (measured from 25° C. to 500° C.).

2. The composition of claim 1, wherein the average leucite crystallite diameter is less than about 3 microns.

3. The composition of claim 1, wherein the average leucite crystallite diameter is between about 1 and about 3 microns.

4. The composition of claim 1, further comprising at least one of 0–1% BaO, 0–4%MgO, 0–3% $Cs_2O$, or 0–1% $CeO_2$ 5. A composition for the manufacture of a dental porcelain, comprising:

62.7% $SiO_2$, 10.11% $Al_2O_3$, 11.0% $K_2O$, 10.3% $Na_2O$, 1.2% $Li_2O$, 1.5% $B_2O_3$, 1.6% CaO, 0.9% MgO, 1.2% F and wherein the porcelain comprises:

a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 870° C. and a coefficient of thermal expansion in the range from about 12 to about $15 \times 10^{-6}/°C$. (measured from 25° C. to 470° C.).

6. A composition for the manufacture of a dental porcelain, comprising

58–65% $SiO_2$, 6–12% $Al_2O_3$, 5.5–18% $K_2O$, 7–12% $Na_2O$, 1.5–3% $Li_2O$, 0.5–4% $B_2O_3$, and 1.2–2.5% CaO, 0–2% F, 0–3% $P_2O_5$, 0.1–1.0% $Sb_2O_3$ and 0.1–2% $CeO_2$ by weight of the total composition, wherein the weight percent of ($F+B_2O_3+P_2O_5$) is in the range from 0.5–4.0 and the weight percent of ($Li_2O$+$Na_2O$) is in the range from 8.5–15, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}$/°C. (measured from 25° C. to 500° C).

7. The composition of claim 6, wherein the average leucite crystallite diameter is less than about 3 microns.

8. The composition of claim 6, wherein the average leucite crystallite diameter is between about 1 and about 3 microns.

9. The composition of claim 6, further comprising at least one of

0–2% BaO, 0–7% MgO, or 0–3% $Cs_2O$.

10. A composition for the manufacture of a dental porcelain, comprising

58–65% $SiO_2$, 6–13% $Al_2O_3$, 5–15% $K_2O$, 7–12% $Na_2O$, 1.5–3% $Li_2O$, 0.5–4% $B_2O_3$, 1.2–2.5% CaO, 0–2% F, 0–3% $P_2O_5$, 0.1–1% $Sb_2O_3$ and 0.1–2% $CeO_2$ by weight of the total composition, wherein the weight percent of (F+$B_2O_3$+$P_2O_5$) is in the range from 0.5–4.0 and the weight percent of ($Li_2O$+$Na_2O$) is in the range from 8.5–15, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}$/°C. (measured from 25° C. to 500° C.).

11. The composition of claim 10, wherein the average leucite crystallite diameter is less than about 3 microns.

12. The composition of claim 10, wherein the average leucite crystallite diameter is between about 1 and about 3 microns.

13. The composition of claim 10, further comprising at least one of

0–2% BaO, 0–7% MgO, or 0–3% $Cs_2O$.

14. A composition for the manufacture of a dental porcelain, comprising 62.0% $SiO_2$, 11.7% $Al_2O_3$, 15.8% $K_2O$, 4.7% $Na_2O$, 2.6% $Li_2O$, 0.5% $B_2O_3$, 1.7% CaO, 0.8% MgO, and 0.5% F by weight of the total composition, wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}$/°C. (measured from 25° C. to 500° C.).

15. A composition for the manufacture of a dental porcelain, comprising 61.5% $SiO_2$, 9.7% $Al_2O_3$, 14.0% $K_2O$, 6.6% $Na_2O$, 2.2% $Li_2O$, 0.9% $B_2O_3$, 1.7% CaO, 0.7% MgO, 0.9% F and 2.1% $Cs_2O$ by weight of the total composition, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}$/°C. (measured from 25° C. to 500° C.).

16. A glassy powder for forming a porcelain comprising 63.2% $SiO_2$, 9.7% $Al_2O_3$; 15.3% $K_2O$, 7.5% $Na_2O$, 1.2% $Li_2O$, 1.1% CaO, 1.1%MgO, and 1.8% F by weight of the total composition, wherein the porcelain is formed by surface crystallization of the glassy powder wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}$/°C. (measured from 25° C. to 500° C.).

17. A glassy powder for the manufacture of a dental porcelain comprising 64.4% $SiO_2$, 9.0% $Al_2O_3$, 13.8% $K_2O$, 8.2% $Na_2O$ 1.2% $Li_2O$, 1.2% CaO, 1.1% MgO, and 2.0% F by weight of the total composition, wherein the porcelain is manufactured by surface crystallization of the glassy powder, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range form about 600° C. to about 885° C. and a coefficient of thermal expansion in the range from about 11 to about $19 \times 10^{-6}$/°C. ( measured from 25° to 500° C.).

18. A dental restoration comprising the porcelain of claim 1.

19. A dental restoration comprising the porcelain of claim 6.

20. A dental restoration comprising the porcelain of claim 10.

21. A method for making a dental porcelain from a single frit porcelain, comprising forming a dental porcelain powder from a dental composition comprising 40–65% $SiO_2$, 6–13% $Al_2O_3$, 5.5–15% $K_2O$, and 6–12% $Na_2O$, 0.5–3% $Li_2O$, 0–4% $B_2O_3$, 0–2% F, and 0.8–2.3 CaO by weight of the total composition, wherein the weight percent of (F+$B_2O_3$) is in the range from 0.8–4.0 and the weight percent of ($Li_2O$+$Na_2O$) is in the range from 4.5–15, and wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}/°C$. (measured from 25° C. to 500° C.);

shaping the dental porcelain powder; and heating the shaped dental porcelain powder to between about 600° C. to about 885° C. to fuse the dental porcelain powder.

22. The method of claim 21, wherein the dental porcelain powder is fused to a ceramic core or a metal framework.

23. A method for making a dental porcelain, forming a dental porcelain powder from a dental composition comprising 62.0% $SiO_2$, 11.7% $Al_2O_3$, 15.8% $K_2O$, 4.7% $Na_2O$, 2.6% $Li_2O$, 0.5% $B_2O_3$, 1.7% CaO, 0.8% MgO, and 0.5% F, by weight of the total composition, wherein the porcelain comprises a glassy matrix phase and a leucite crystallite phase, wherein the leucite phase comprises from about 5 to about 65% by weight of the total composition and the leucite crystallites have average diameters of less than about 7 microns; and further wherein the porcelain has a maturing temperature in the range from about 600° C. to about 885° C. and a coefficient of thermal expansion in the range from about 11 to about $19 \times 10^{-6}/°$ C. (measured from 25° C. to 500° C.);

shaping the dental porcelain powder; and heating the shaped dental porcelain powder to between about 600° C. to about 885° C. to fuse the dental porcelain powder.

24. A composition for the manufacture of a dental porcelain, comprising a porcelain composition having $Cs_2O$ and a molar ratio of $Cs_2O/K_2O$ of less than 0.1;

a coefficient of thermal expansion in the range from about 11 to about $19 \times 10^{-6}/°C$. (measured from 25° C. to 500° C.), said coefficient of thermal expansion being comparable to or greater than the same porcelain composition having a lesser weight percent of $Cs_2O$; and a weight percent of leucite lesser than the same porcelain composition having a lesser weight percent of $Cs_2O$.

25. A method for the manufacture of a leucite-containing porcelain composition, comprising formulating a porcelain composition so as to have $Cs_2O$ and a molar ratio of $Cs_2O/K_2O$ of less than 0.1, thereby resulting in a porcelain composition having a coefficient of thermal expansion in the range from about 11 to about $19 \times 10^{-6}/°C$. (measured from 25° C. to 500° C.), said coefficient of thermal expansion being comparable to or greater than the same porcelain composition having a lesser weight percent of $Cs_2O$; and a lesser weight percent of leucite than the same porcelain composition having a lesser weight percent of $Cs_2O$.

* * * * *